(12) United States Patent
Jue et al.

(10) Patent No.: US 8,741,119 B1
(45) Date of Patent: Jun. 3, 2014

(54) ACTINIDE ION SENSOR FOR PYROPROCESS MONITORING

(75) Inventors: Jan-fong Jue, Idaho Falls, ID (US); Shelly X. Li, Idaho Falls, ID (US)

(73) Assignee: U.S. Department of Energy, Washington, DC (US)

( * ) Notice: Subject to any disclaimer, the term of this patent is extended or adjusted under 35 U.S.C. 154(b) by 740 days.

(21) Appl. No.: 13/039,451

(22) Filed: Mar. 3, 2011

(51) Int. Cl.
*G01N 27/406* (2006.01)

(52) U.S. Cl.
USPC ........... 204/415; 204/416; 204/419; 204/422; 205/43

(58) Field of Classification Search
USPC .......................................................... 204/415
See application file for complete search history.

(56) References Cited

U.S. PATENT DOCUMENTS

| | | | |
|---|---|---|---|
| 4,085,023 A * | 4/1978 | Fray | 204/422 |
| 4,098,651 A | 7/1978 | Alder | |
| 4,585,635 A | 4/1986 | Hellstrom | |
| 4,645,571 A * | 2/1987 | Dubreuil et al. | 205/781.5 |
| 4,664,849 A | 5/1987 | Farrington et al. | |
| 4,808,827 A | 2/1989 | Woollam | |
| 4,814,062 A * | 3/1989 | Redey et al. | 204/420 |
| 4,880,506 A | 11/1989 | Ackerman et al. | |
| 5,009,752 A | 4/1991 | Tomczuk et al. | |
| 5,348,626 A * | 9/1994 | Miller et al. | 205/44 |
| 5,474,959 A | 12/1995 | Schafer et al. | |
| 5,552,025 A * | 9/1996 | Coe | 205/785.5 |
| 5,582,706 A | 12/1996 | Grantham et al. | |
| 6,514,394 B1 * | 2/2003 | Vangrunderbeek et al. | 204/400 |
| 7,267,754 B1 | 9/2007 | Willit | |
| 7,390,392 B1 * | 6/2008 | Choi et al. | 205/781.5 |
| 7,799,185 B1 | 9/2010 | Willit | |

* cited by examiner

*Primary Examiner* — Bryan D. Ripa
(74) *Attorney, Agent, or Firm* — Michael J. Dobbs; Daniel Park; John T. Lucas

(57) ABSTRACT

An apparatus for real-time, in-situ monitoring of actinide ion concentrations which comprises a working electrode, a reference electrode, a container, a working electrolyte, a separator, a reference electrolyte, and a voltmeter. The container holds the working electrolyte. The voltmeter is electrically connected to the working electrode and the reference electrode and measures the voltage between those electrodes. The working electrode contacts the working electrolyte. The working electrolyte comprises an actinide ion of interest. The reference electrode contacts the reference electrolyte. The reference electrolyte is separated from the working electrolyte by the separator. The separator contacts both the working electrolyte and the reference electrolyte. The separator is ionically conductive to the actinide ion of interest. The reference electrolyte comprises a known concentration of the actinide ion of interest. The separator comprises a beta double prime alumina exchanged with the actinide ion of interest.

17 Claims, 4 Drawing Sheets

ACTINIDE ION SENSOR FOR PYROPROCESS MONITORING

GOVERNMENT INTERESTS

The United States Government has rights in this invention pursuant to Contract No. DE-AC07-051D14517, between the U.S. Department of Energy (DOE) and Battelle Energy Alliance.

FIELD OF THE INVENTION

One embodiment of the present invention relates to a real-time, in-situ sensor for monitoring actinide ion concentrations in electrolyte, preferably plutonium, in the molten salt electrolyte for pyroprocessing of spent nuclear fuel.

BACKGROUND OF THE INVENTION

Nuclear reactors are becoming an increasingly necessary means of meeting the nation's energy requirements given growing concerns about traditional carbon producing methods of generating energy. A principal concern prior to the acceptance of nuclear energy is the safe management of radioactive waste during reprocessing and storage.

This concern is addressed is by utilizing nuclear reprocessing techniques, such as pyroprocessing, to extract nuclear components from the spent fuel discharged from reactors. Pyroprocessing involves dissolving spent fuel at high temperatures in a molten salt to create a molten salt electrolyte. Then the spent fuel is electrorefined in the molten salt, which essentially electroplates most or all of the actinides elements for extraction. Typically, a solid metal cathode is used to extract uranium and a liquid cadmium cathode is used to extract all actinides, including plutonium. Plutonium and uranium are focused upon because the other transuranic elements exist at much lower concentrations in the molten salt electrolyte.

In pyroprocessing, the electrorefining process must be carefully monitored to ensure that the electrochemical operation is proceeding efficiently. Specifically, monitoring the concentration ratio of $Pu^{3+}$ to $U^{3+}$ in the molten salt electrolyte is particularly important because electrorefining operators need to know which extraction technique is optimal. For example, the solid metal cathode is operated; uranium is extracted from the molten salt electrolyte and the $Pu^{3+}$ to $U^{3+}$ ratio increases. The solid metal cathode becomes increasingly inefficient as the $Pu^{3+}$ to $U^{3+}$ ratio increases, at which point it may become preferable to switch from operating the solid metal cathode to operating a liquid cadmium cathode. Similarly, as the liquid cadmium cathode is used, plutonium is extracted from the molten salt electrolyte. The continued use of the liquid cadmium cathode becomes increasingly inefficient as the $Pu^{3+}$ to $U^{3+}$ ratio decreases.

As a result, monitoring the $Pu^{3+}$ and $U^{3+}$ concentrations in the molten salt electrolyte is important to ensure that the refining process is efficient at collecting actinides. The current method for measuring actinides in molten salt electrolytes involves taking a sample of the highly radioactive molten salt electrolyte, transferring that radioactive sample to a laboratory, and analyzing the sample using an inductively coupled plasma mass spectrometer (ICP-MS). Sadly, the entire process generally requires a few weeks before results are obtained. Therefore, there exists a need for in-situ, real-time monitoring of actinide ion concentrations in molten salt electrolyte for pyroprocessing.

SUMMARY OF THE INVENTION

An apparatus for real-time, in-situ monitoring of actinide ion concentrations which comprises a working electrode, a reference electrode, a container, a working electrolyte, a separator, a reference electrolyte, and a voltmeter. The container holds the working electrolyte. The voltmeter is electrically connected to the working electrode and the reference electrode and measures the voltage between those electrodes. The working electrode contacts the working electrolyte. The working electrolyte comprises an actinide ion of interest. The reference electrode contacts the reference electrolyte.

The reference electrolyte is separated from the working electrolyte by the separator. The separator contacts both the working electrolyte and the reference electrolyte. The separator is ionically conductive to the actinide ion of interest. The reference electrolyte comprises the actinide ion of interest with fixed concentration. The separator comprises a beta double prime alumina exchanged with the actinide ion of interest.

DETAILED DESCRIPTION OF THE INVENTION

An apparatus for real-time, in-situ monitoring of actinide ion concentrations which comprises a working electrode, a reference electrode, a container, a working electrolyte, a separator, a reference electrolyte, and a voltmeter. The container holds the working electrolyte. The voltmeter is electrically connected to the working electrode and the reference electrode and measures the voltage between those electrodes. The working electrode contacts the working electrolyte. The working electrolyte comprises an actinide ion of interest. The reference electrode contacts the reference electrolyte.

The reference electrolyte is separated from the working electrolyte by the separator. The separator contacts both the working electrolyte and the reference electrolyte. The separator is ionically conductive to the actinide ion of interest. The reference electrolyte comprises the actinide ion of interest with fixed concentration. The separator comprises a beta double prime alumina exchanged with the actinide ion of interest.

FIG. 1

Figure 1:
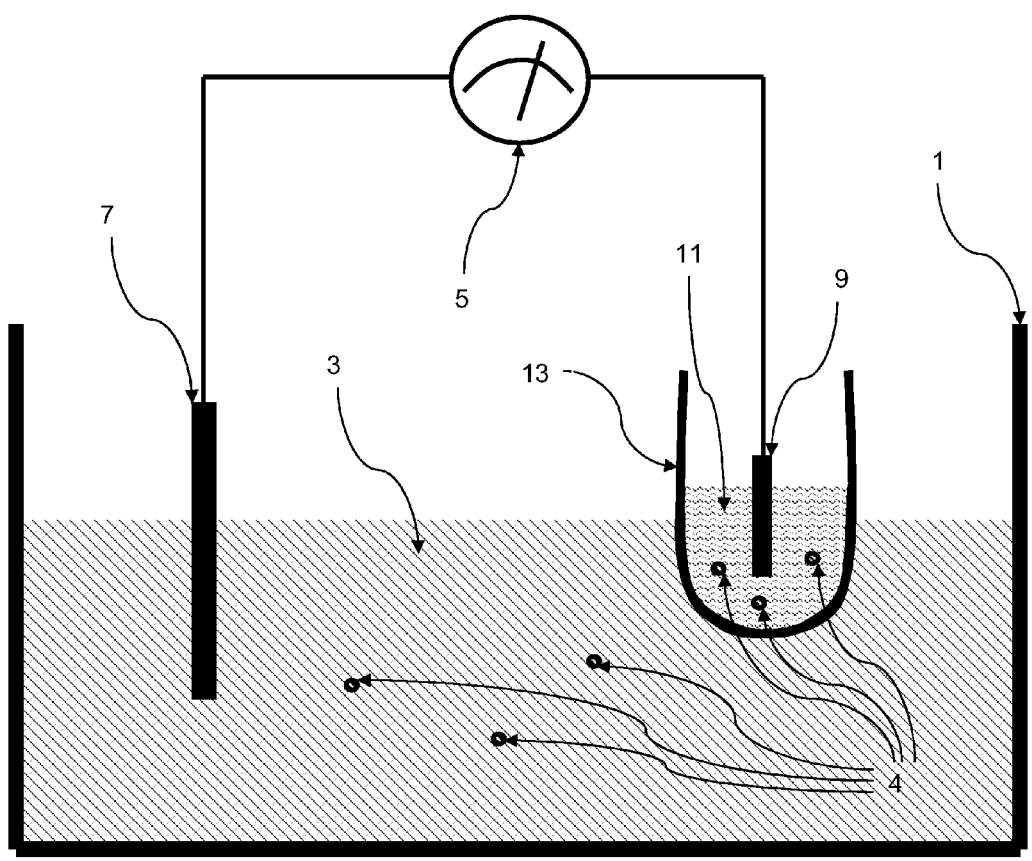
FIG. 1 shows a cross sectional view of one embodiment of an actinide ion sensor for pyroprocess monitoring.

FIG. 1 shows a cross sectional view of one embodiment of an actinide ion sensor for pyroprocess monitoring. Shown is a container 1 holding a working electrolyte 3; the working electrolyte 3 comprising an actinide ion of interest 4. Additionally, a voltmeter 5 is electrically connected to a working electrode 7 and a reference electrode 9. The working electrode 7 contacts the working electrolyte 3. Preferably, the working electrode 7 is submerged in the working electrolyte 3, more preferably, the majority of the working electrode 7 is submerged in the working electrolyte 3.

The reference electrode 9 contacts a reference electrolyte 11. The reference electrolyte 11 comprises the actinide ion of interest 4. Preferably, the reference electrode 9 is submerged in the reference electrolyte 11, more preferably, the majority of the reference electrode 9 is submerged in the reference electrolyte 11.

The reference electrolyte 11 is separated from the working electrolyte 3 by a separator 13. The separator 13 contacts both the working electrolyte 3 and the reference electrolyte 11. The separator 13 is submerged in the working electrolyte 3, more preferably, the majority of the separator 13 is submerged in the working electrolyte 3. The separator 13 comprises a beta double prime alumina exchanged with the actinide ion of interest 4. The separator 13 conducts the actinide ion of interest 4 between the working electrolyte 3 and the reference electrolyte 11. The voltmeter 5 measure the voltage between the reference electrode 9 and the working electrode 7.

Container 1

The container 1 is comprised of any material that does not substantially react with the working electrolyte 3 during pyroprocessing. Preferably, the material does not substantially react if the material is used continually for over one year without damage or need of repair or replacement of equipment. More preferably, the container 1 is stainless steel, ceramic (e.g. $Al_2O_3$), or a combination thereof container, which is capable of withstanding the high temperature, corrosive, and radioactive environment present during pyroprocessing.

Working Electrolyte 3

The working electrolyte 3 is any substance comprising free ions of the actinide ion of interest 4. Preferably, the working electrolyte 3 is a molten salt electrolyte having free ions of an actinide ion of interest 4, preferably $Pu^{3+}$ and $U^{3+}$. Preferably, the molten salt electrolyte is a chloride or fluoride salt, more preferably a LiCl—KCl eutectic mixture, preferably heated to greater than 450 degrees centigrade. In a preferred embodiment, the working electrolyte 3 is $3LiCl_2$-$2KCl_2$. Preferably, the working electrolyte 3 comprises $PuCl_3$ and $UCl_3$. In alternative embodiments, other salt mixtures, such as LiF—$CaF_2$ and LiCl—$Li_2O$ with corresponding plutonium ions at the above their melting temperatures, are utilized.

Actinide Ion of Interest 4

The actinide ion of interest 4 is an ion or charged molecule comprising at least one of the elements in spent nuclear fuel, which include: Thorium, Uranium, Neptunium, Plutonium, Americium, and Curium. Preferably, the actinide ion of interest 4 is Neptunium, Plutonium, and Americium. More preferably, the actinide ion of interest 4 is $Pu^{3+}$.

Voltmeter 5

The voltmeter 5 is any device used to determine or indicate the voltage across the working electrode 7 and reference electrode 9, which is related to the concentration of actinide ion of interest 4 in the working electrolyte 3. Exemplary embodiments of the voltmeter 5 include a multimeter, a potentiometer, a galvanometer, an oscilloscope, and an analog-to-digital converter. Preferably, the voltmeter 5 comprises one or more electrical components, more preferably a central processing unit, microcontroller, application specific integrated circuit (ASIC), an analog-to-digital converter, a voltage comparator or combinations thereof. In a preferred embodiment, the voltmeter 5 is an analog-to-digital converter connected to a microcontroller/central-processing-unit (CPU) having a display (e.g. FIG. 3). In an alternative embodiment, the voltmeter 5 is an electrical circuit configured to output light in relation to voltage across the working electrode 7 and reference electrode 9 (e.g. FIG. 4). Preferably, the voltmeter 5 provides a high-impedance across the working electrode 7 and reference electrode 9 as close to an open circuit (infinite impedance) as possible, to prevent any electrical current between the working electrode 7 and the reference electrode 9.

Working Electrode 7

The working electrode 7 is made from any electrically conductive material which is not substantially reactive with the working electrolyte 3. Preferably, the material is not substantially reactive if the material is used continually for over one year without damage or need of repair or replacement of equipment. More preferably, the working electrode 7 is made of tantalum, tungsten, platinum, or a combination thereof.

Reference Electrode 9

The reference electrode 9 is made from any electrically conductive material which is not substantially reactive with the ionic environment of the reference electrolyte 11. Preferably, the material is not substantially reactive if the material is used continually for over one year without damage or need of repair or replacement of equipment. More preferably, the reference electrode 9 is made of tantalum, tungsten, platinum, or a combination thereof.

Reference Electrolyte 11

The reference electrolyte 11 is a compound or solution with a known concentration of the actinide ion of interest 4. Preferably, the reference electrolyte 11 is any substance comprising free ions of the actinide ion of interest 4. In one embodiment, the reference electrolyte 11 comprises molten salts with known plutonium ion concentrations. In yet another alternative embodiment, the reference electrolyte 11 may further comprise liquid metal with dissolved plutonium or intermetallics, preferably Pu—Cd or Pu—Bi solutions which are saturated with Pu.

Separator 13

The separator 13 is made into a configuration sufficient to separate the reference electrolyte 11 from the working electrolyte 3 and ionically conductive to the actinide ion of interest 4. Ionically conductive refers to ionic conduction of the actinide ion of interest 4 through all, or a portion, of the separator 13. Preferably, the separator 13 has an ionic conductivity to the actinide ion of interest 4 greater than $10^{-6}$ S/cm. Preferably, the separator 13 is made into a tube with a single closed end. In an alternative embodiment, the separator 13 is made from a disk cemented to one open end of a tube. Other shapes and configuration may also be used. Preferred embodiments encompass a separator 13 made from a plurality of portions, whereby one or more of the plurality of portions are ionically conductive to the actinide ion of interest 4.

The separator 13 comprises beta double prime alumina exchanged with the actinide ion of interest 4. Preferably, the exchanged beta double prime alumina is created by a vapor or molten phase exchange, or both, between sodium beta double prime alumina and a salt comprising the actinide (ion or neutral) of the actinide ion of interest 4. In one embodiment, the phase exchange occurs directly. In an alternative embodiment, the phase exchange occurs with one or more intermediate exchanges with other elements. Preferably, the beta double prime alumina exchanged with the actinide of the actinide ion of interest 4 is created by the vapor or molten phase exchange, or both, between sodium beta double prime alumina and the actinide salt $PuCl_3$.

In one embodiment, the exchanged beta double prime alumina is made by vapor phase exchange using a non-reactive crucible, preferably made of tantalum, alumina, quartz, or a combination thereof. The crucible holds a salt comprising the actinide of the actinide ion of interest 4, and the sodium beta double prime alumina is suspended above the salt. The crucible is then heated to 550-800 degrees centigrade for 24-120 hours. In an alternative embodiment, for molten phase exchange, sodium beta double prime alumina is submerged in the molten phase of a salt comprising the actinide of the actinide ion of interest 4 for 24-120 hours. In both molten and vapor phase exchange, the actinide of the actinide ion of interest 4 from the salt replaces the sodium in the sodium beta double prime alumina resulting in the exchanged beta double prime alumina. Preferably, in alternative embodiments, the exchanged beta double prime alumina is plutonium beta double prime alumina.

FIG. 2

Figure 2:
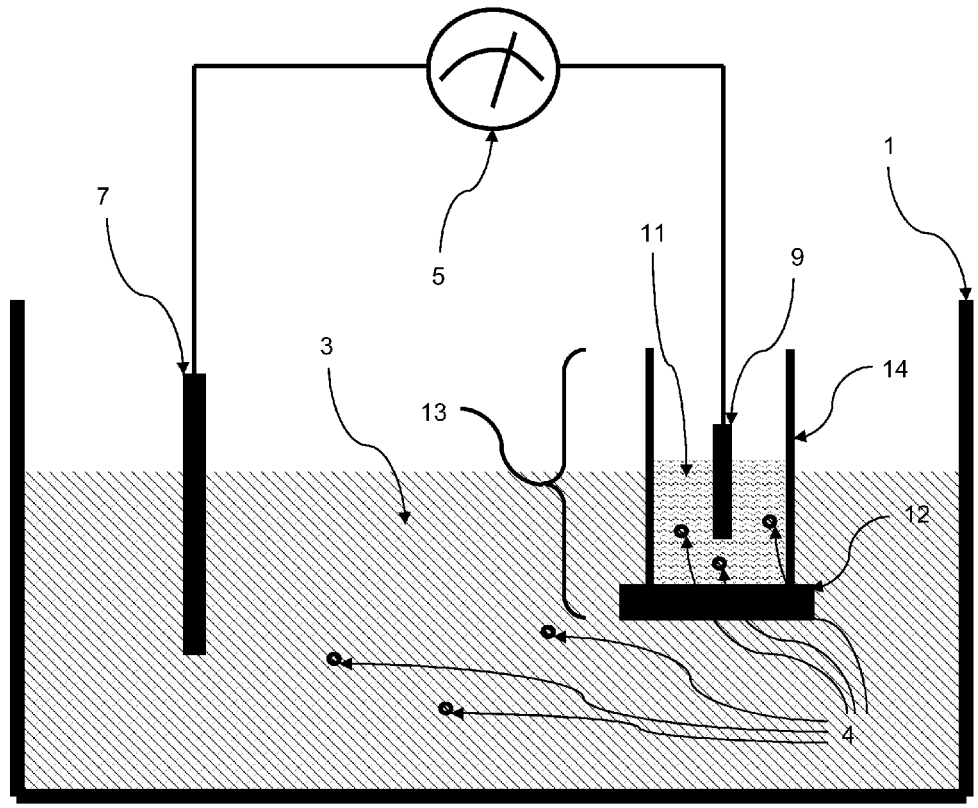
FIG. 2 shows a cross sectional view of one embodiment of the actinide ion sensor for pyroprocess monitoring having a separator made from a disk cemented to one open end of a tube.

FIG. 2 shows a cross sectional view of one embodiment of the actinide ion sensor for pyroprocess monitoring having a separator 13 made from a disk 12 cemented to one open end of a tube 14. In the embodiment shown in FIG. 2, the container 1, working electrolyte 3, actinide ion of interest 4, voltmeter 5, working electrode 7, reference electrode 9, and reference electrolyte 11 are as described above.

Separator 13

In this embodiment, the separator 13 is made into a configuration sufficient to separate the reference electrolyte 11 from the working electrolyte 3 while also ionically conductive to the actinide ion of interest 4. Ionically conductive refers to ionic conduction through all, or a portion, of the separator 13 with respect to the actinide ion of interest 4.

In this embodiment, the separator 13 is made from two portions, a disk 12 and a tube 14. The separator 13 is formed by cementing the disk 12 to one open end of a tube 14. The reference electrolyte 11 is separated from the working electrolyte 3 by the separator 13. Preferably the disk 12 and a tube 14 of the separator 13 form a vessel having an interior comprising the reference electrolyte 11 and an exterior contacting the working electrolyte 3. The separator 13 contacts both the working electrolyte 3 and the reference electrolyte 11. Preferably, the disk 12 contacts the working electrolyte 3. More preferably, the separator 13 is submerged in the working electrolyte 3, so that the disk 12 is fully submerged in the working electrolyte 3, and the tube 14 contacts the working electrolyte 3. Yet more preferably, the separator 13 is submerged in the working electrolyte 3, so that the disk 12 is fully submerged in the working electrolyte 3, and the majority of the tube 14 is submerged in the working electrolyte 3.

In one embodiment, the disk 12 is made of a material comprising beta double prime alumina exchanged with the actinide ion of interest 4 and the tube 14 is made from a material that does not substantially conduct the actinide ion of interest 4. Preferably, the material that does not substantially conduct the actinide ion of interest 4 is $Al_2O_3$. The result is a separator 13 in which substantially all ionic conduction with respect to the actinide ion of interest 4 occurs through the disk 12.

In an alternative embodiment, both the disk 12 and the tube 14 are made from an actinide ion of interest 4 conducting material, preferably comprising beta double prime alumina exchanged with the actinide ion of interest 4. The result is a separator 13 in which ionic conduction with respect to the actinide ion of interest 4 occurs through portions of the disk 12, portions of the tube 14, or a combination thereof.

In an alternative embodiment, the tube 14 is made of a material comprising beta double prime alumina exchanged with the actinide ion of interest 4 and the disk 12 is made from a material that does not substantially conduct the actinide ion of interest 4. Preferably, the material that does not substantially conduct the actinide ion of interest 4 is $Al_2O_3$. The result is a separator 13 in which substantially all ionic conduction with respect to the actinide ion of interest 4 occurs through the tube 14.

In an alternative embodiment, the separator 13 is made from a plurality of actinide ion of interest 4 conductors and actinide ion of interest 4 substantially non-conductor portions. At least one actinide ion of interest 4 conductor portion contacts both the working electrolyte 3 and the reference electrolyte 11. Preferably, the material that does not substantially conduct the actinide ion of interest 4 is $Al_2O_3$.

FIG. 3

Figure 3:
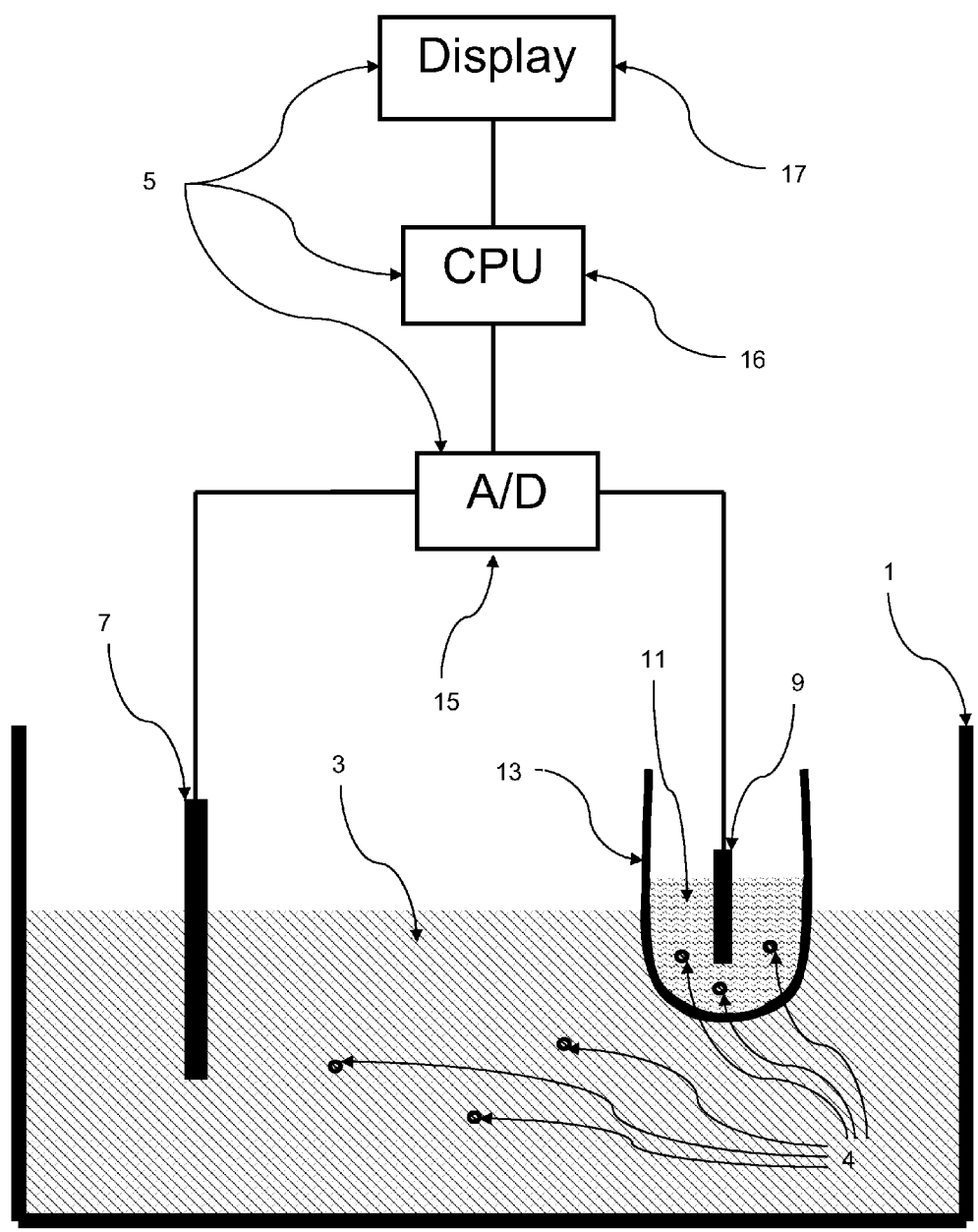
FIG. 3 shows a cross sectional view of one embodiment of the actinide ion sensor for pyroprocess monitoring whereby the voltmeter comprises an analog-to-digital converter, a CPU, and a display.

FIG. 3 shows a cross sectional view of one embodiment of the actinide ion sensor for pyroprocess monitoring whereby the voltmeter 5 comprises an analog-to-digital converter 15, a central processing unit (CPU) 16, and a display 17, as a means for displaying the actinide ion of interest 4 concentration. In this embodiment, the container 1, working electrolyte 3, actinide ion of interest 4, voltmeter 5, working electrode 7, reference electrode 9, reference electrolyte 11, and separator 13 are as described above.

Voltmeter 5

In this embodiment, the voltmeter 5 comprises an analog-to-digital converter 15, a CPU 16, and a display 17. Preferably, the communication between the analog-to-digital converter 15 the CPU 16, and the display 17 is accomplished via one or more wires, busses, wireless communication technologies, etc. In a preferred embodiment, the CPU 16 is connected to the analog-to-digital converter 15 and the display 17 via one or more wires.

CPU 16

The CPU 16 is any means for calculating the actinide ion of interest 4 concentration in the working electrolyte 3, more preferably a personal computer, a laptop, a microcontroller, or an application-specific integrated circuit (ASIC). Preferably, the CPU 16 comprises a microcontroller having a built-in analog-to-digital converter 15, for example, the microcontroller manufactured by Atmel sold under the trademark ATMEGA128. In an alternate embodiment, the CPU 16 comprises a comparator (e.g. LM339).

The CPU 16 calculates the relative or absolute actinide ion of interest 4 concentration in the working electrolyte 3 from the voltage measured by the analog-to-digital converter 15. In one embodiment, the calculated actinide ion of interest 4 calculation is absolute, meaning the actinide ion of interest 4 concentration in the working electrolyte 3. In an alternative embodiment, the calculated actinide ion of interest 4 is a relative value, meaning the actinide ion of interest 4 concentration with respect to a reference solution comprising the actinide ion of interest 4, or with respect to a specified actinide ion of interest 4 concentration or concentration range. In one embodiment, the specified actinide ion of interest 4 concentration or concentration range is coded into the programming. In an alternative embodiment, the specified actinide ion of interest 4 concentration or concentration range is inputted by the user through a user interference, for example a keyboard, touch screen or dial.

Preferably, the actinide ion of interest 4 concentration in the working electrolyte 3 is calculated using the Nernst equation, which can be written to relate the measured voltage, E, to the unknown mole fraction of the actinide ion of interest 4 in the working electrolyte 3, $X_M(WE)$, as shown in Eq. 1:

$$E = E^0 - \left(\frac{RT}{ZF}\right)\ln[\gamma_M^0(WE)] - \left(\frac{RT}{ZF}\right)\ln[X_M(WE)] + A \quad (Eq.\ 1)$$

where, $E^0$ is the standard electrode potential for the cell, R is the gas constant, T is the temperature in Kelvin, Z is the charge of the actinide ion of interest 4, F is Faraday's constant, A is constant, and $Y_M^0(WE)$ is activity coefficient of the actinide ion of interest in the working electrolyte 3. The mole fraction indicates the actinide ion of interest 4 concentration because it is the number of moles of the actinide ion of interest 4 over the total moles of the solution.

In an alternative embodiment, the CPU 16 calculates the actinide ion of interest 4 concentration in the working electrolyte 3 as discussed above, but also compares the calculated concentration value to a target concentration, concentration range, or calibration curve. In one embodiment, the target concentration or concentration range is coded into the programming. In an alternative embodiment, the target concentration or concentration range is input by the user.

In an alternative embodiment, the voltage between the reference electrode 9 and the working electrode 9, detected by the analog-to-digital converter 15 is communicated to the CPU 16. The CPU 16 compares the voltage measurement to a target voltage or specified voltage range. In one embodiment, the target voltage or specified voltage range is coded into the programming. In an alternative embodiment, the target voltage or specified voltage range is input by the user.

Display 17

The CPU 16 communicates the calculated actinide ion of interest 4 concentration to the display 17 to be displayed. Preferably, the display 17 is a personal computer display, a laptop display, a digital display, an LED display, a segment LED display, one or more LED displays, etc. Preferably, a relative ratio of the actual concentration of actinide ion of interest 4 to a predetermined maximum, an absolute value of the concentration of actinides of interest 4, or a combination thereof is displayed by the display 17.

In one embodiment, the display 17 is a light that activates, deactivates, or blinks, one or more times, based upon a communication received from the CPU 16. Preferably, the light is an incandescent bulb, an LED, a fluorescent lamp, or similar photon emitting device.

FIG. 4

Figure 4:
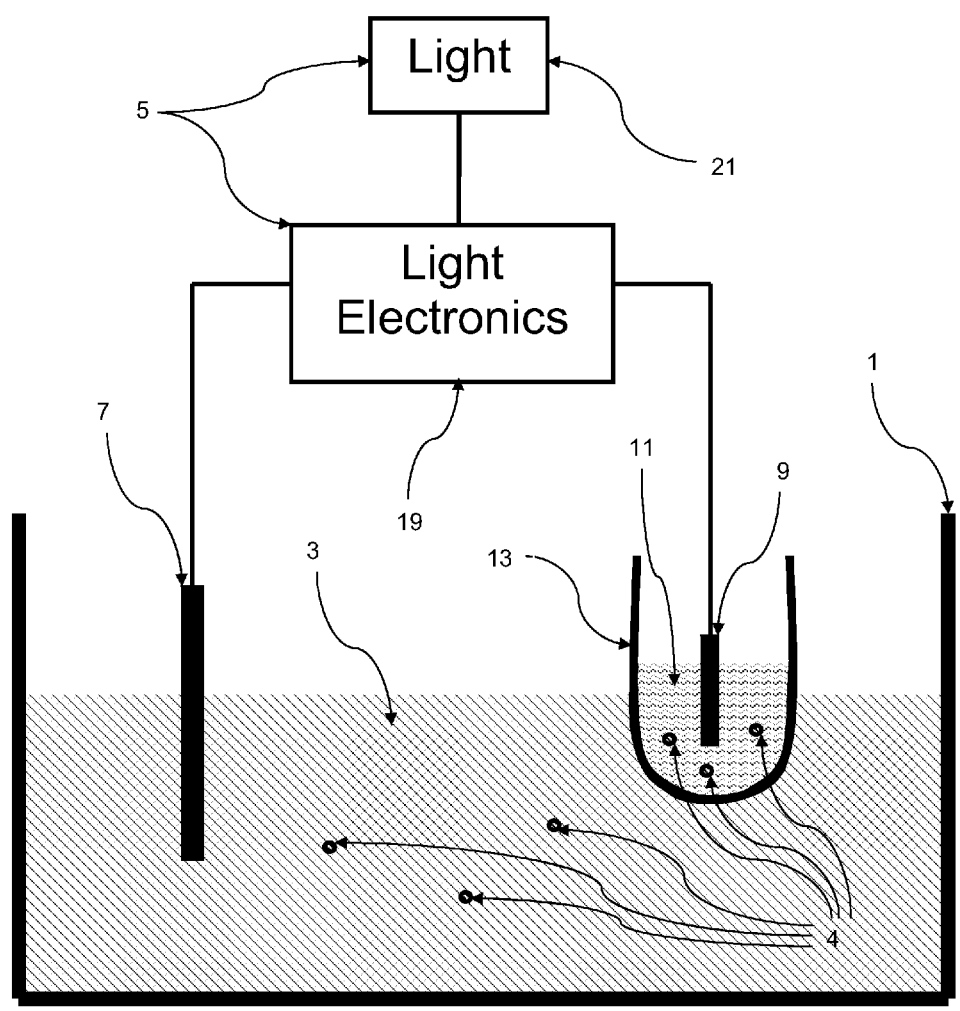
FIG. 4 shows a cross sectional view of one embodiment of the actinide ion sensor for pyroprocess monitoring whereby the voltmeter comprises a light.

FIG. 4 shows a cross sectional view of one embodiment of the actinide ion sensor for pyroprocess monitoring whereby the voltmeter 5 comprises light electronics 19 and a light 21 to indicate the actinide ion of interest 4 concentration in the working electrolyte 3. In this embodiment, the container 1, working electrolyte 3, actinide ion of interest 4, working electrode 7, reference electrode 9, reference electrolyte 11, and separator 13 are as described above.

Light Electronics 19

In this embodiment, light electronics 19 are electrically connected to the working electrode 7, the reference electrode 9, and the light 21. The light electronics 19 provide a high-impedance across the working electrode 7 and reference electrode 9, preferably, using one or more operational amplifiers. In a preferred embodiment, the light electronics 19 comprises a voltage comparator (e.g. LM339).

In one embodiment, a buffered operational amplifier is implemented to provide a high-impedance across the working electrode 7 and reference electrode 9. In a preferred embodiment, an inverting or non-inverting operational amplifier is used to provide a high-impedance across the working electrode 7 and reference electrode 9 while also amplifying the voltage/current to be sufficient for powering the light 21. In one embodiment, the light electronics 19 further comprises a means for amplifying or attenuating the voltage supplied to the light 21, for example, a voltage divider, an operational amplifier, one or more transistors, or a combination thereof.

Light 21

Preferably, the light 21 is an incandescent bulb, an LED, a fluorescent lamp, or similar photon emitting device.

In one embodiment, the light 21 increases in brightness as the actinide ion of interest 4 concentration decreases in the working electrolyte 3. As the actinide ion of interest 4 is removed from the working electrolyte 3 during pyroprocessing, the actinide ion of interest 4 concentration decreases while the actinide ion of interest 4 concentration in the reference electrolyte 11 remains stable. As a result, the voltage increases between the working electrode 7 and the reference electrode 9, increasing the brightness of the light 21 as more of the actinide ion of interest 4 is removed during pyroprocessing. In an alternate embodiment, an inverter circuit provides for an increase light as concentration of the actinide ion of interest increases. In an alternative embodiment, the light 21 includes a threshold circuit (passive or active that does not supply voltage to the light 21 unless a specified voltage is exceeded. For example, a voltage comparator (e.g. LM 339) or Zener diode connected in reverse polarity may be used to light the light 21 when a predetermined voltage is exceeded. Preferably, one or more resistors creating a voltage divider is used to optimize the circuit.

In a preferred embodiment, user input is used to indicate when the light 21 is toggled on or off. For example, a potentiometer may be used to produce a reference voltage depended on the position of the potentiometer that is feed into a comparator (e.g. LM339) with the voltage between the voltage across the working electrode 7 and reference electrode 9. Preferably, the reference electrode 9 is used as a system ground. Depending on the position of the potentiometer, the light 21 may be power on/off at different actinide ion of interest 4 concentrations.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

All publications and patent documents cited in this application are incorporated by reference in their entirety for all purposes to the same extent as if each individual publication or patent document were so individually denoted.

Any element in a claim that does not explicitly state "means for" performing a specified function, or "step for" performing a specific function, is not to be interpreted as a "means" or "step" clause as specified in 35 U.S.C.§112, ¶ 6. In particular, the use of "step of" in the claims herein is not intended to invoke the provisions of 35 U.S.C.§112, ¶ 6.

We claim:
1. An apparatus for real-time monitoring of actinide ion concentrations in molten salts, comprising:
   a) a working electrode, a reference electrode, a container, a working electrolyte, a separator, a reference electrolyte, and a voltmeter;
   b) said working electrolyte comprising an actinide ion of interest;
   c) said container holding said working electrolyte;
   d) said separator separating and contacting said working electrolyte and said reference electrolyte;
   e) said working electrolyte contacting said working electrode;
   f) said separator ionically conductive to said actinide ion of interest;
   g) said reference electrode contacting said reference electrolyte;
   h) said reference electrolyte comprising said actinide ion of interest with a known concentration;
   i) said separator comprising beta double prime alumina exchanged with said actinide ion of interest;
   j) said voltmeter electrically connected to said working electrode and said reference electrode; and
   k) said voltmeter having a means for measuring the voltage between said working electrode and said reference electrode; and
   l) said voltmeter having a means for indicating the concentration of said actinide ions of interest within said working electrolyte.
2. The apparatus of claim 1, further comprising:
   a) said voltmeter having a means for determining the concentration of said actinide ions of interest within said working electrolyte from said measured voltage between said working electrode and said reference electrode;
   b) said voltmeter comprising a central processing unit, microcontroller, application specific integrated circuit (ASIC), an analog-to-digital converter, a voltage comparator or combinations thereof.
3. The apparatus of claim 1, further comprising:
   a) said working electrode comprises tantalum, platinum, tungsten, or a combination thereof; and
   b) said reference electrode comprises tantalum, platinum, tungsten, or a combination thereof.
4. The apparatus of claim 1, wherein said working electrolyte comprises a molten salt electrolyte.

5. The apparatus of claim 1, wherein said working electrolyte comprises LiCl—KCl.
6. The apparatus of claim 1, wherein said working electrolyte comprises LiCl—KCl—$UCl_3$—$PuCl_3$.
7. The apparatus of claim 1, wherein said actinide ion of interest is plutonium.
8. The apparatus of claim 1, wherein said separator comprises:
   a) one or more actinide ion of interest conducting portions; and
   b) said one or more actinide ion of interest conducting portions comprising beta double prime alumina exchanged with said actinide ion of interest.
9. The apparatus of claim 2, whereby:
   a) said means for measuring the voltage between said working electrode and said reference electrode comprises an analog-to-digital converter;
   b) said means for determining the concentration of said actinide ions of interest within said working electrolyte comprises a central processing unit;
   c) said means for indicating an concentration of said actinide ions of interest within said working electrolyte comprises a display; and
   d) said central processing unit connected to said analog-to-digital converter and said display.
10. The apparatus of claim 9, wherein said means for determining the concentration of said actinide ions of interest within said working electrolyte comprises a means for calculating the concentration of said actinide ion of interest comprising applying the Nernst equation.
11. The apparatus of claim 1, whereby:
   a) said means for measuring the voltage between said working electrode and said reference electrode and said means for determining the concentration of said actinide ions of interest within said working electrolyte comprises light electronics;
   b) said means for indicating an concentration of said actinide ions of interest within said working electrolyte comprises a light;
   c) said light electronics electrically connected to said reference electrode, said working electrode, and said light; and
   d) said light electronics comprising a means for supplying a voltage to said light in relation to the actinide of interest concentration in said working electrolyte.
12. The apparatus of claim 2, further comprising:
   a) said working electrode comprises tantalum, platinum, tungsten, or a combination thereof; and
   b) said reference electrode comprises tantalum, platinum, tungsten, or a combination thereof.
13. The apparatus of claim 12, wherein said working electrolyte comprises a molten salt electrolyte.
14. The apparatus of claim 13, wherein said working electrolyte comprises LiCl—KCl.
15. The apparatus of claim 14, wherein said actinide ion of interest is plutonium.
16. The apparatus of claim 14, said voltmeter comprising:
   a) said means for measuring the voltage between said working electrode and said reference electrode further comprising said analog-to-digital converter;
   b) said means for determining the concentration of said actinide ions of interest within said working electrolyte further comprising said central processing unit;
   c) said means for indicating the concentration of said actinide ions of interest within said working electrolyte further comprising a display; and d) said central processing unit connected to said analog-to-digital converter and said display.

17. The apparatus of claim 14, wherein said voltmeter comprises:
   a) said means for measuring the voltage between said working electrode and said reference electrode and said means for determining the concentration of said actinide ions of interest within said working electrolyte comprises light electronics;
   b) said means for indicating an concentration of said actinide ions of interest within said working electrolyte comprises a light;
   c) said light electronics electrically connected to said reference electrode, said working electrode, and said light; and
   d) said light electronics comprising a means for supplying a voltage to said light in relation to the actinide of interest concentration in said working electrolyte.

* * * * *